(12) United States Patent
Bang et al.

(10) Patent No.: US 8,399,620 B2
(45) Date of Patent: Mar. 19, 2013

(54) PURIFICATION OF FACTOR VIII USING A MIXED-MODE OR MULTIMODAL RESIN

(75) Inventors: Susanne Bang, Bagsvaerd (DK); Lars Thim, Gentofte (DK); Johan Karlsson, Skurup (SE)

(73) Assignee: Novo Nordisk A/S, Bagsvaerd (DK)

( * ) Notice: Subject to any disclaimer, the term of this patent is extended or adjusted under 35 U.S.C. 154(b) by 435 days.

(21) Appl. No.: 12/668,530

(22) PCT Filed: Jul. 11, 2008

(86) PCT No.: PCT/EP2008/059094
§ 371 (c)(1),
(2), (4) Date: Mar. 26, 2010

(87) PCT Pub. No.: WO2009/007451
PCT Pub. Date: Jan. 15, 2009

(65) Prior Publication Data
US 2010/0204452 A1    Aug. 12, 2010

Related U.S. Application Data

(60) Provisional application No. 60/950,120, filed on Jul. 17, 2007.

(30) Foreign Application Priority Data

Jul. 11, 2007    (EP) .................................... 07112287

(51) Int. Cl.
*C07K 1/16*    (2006.01)
*C07K 1/18*    (2006.01)
*C07K 1/20*    (2006.01)

(52) U.S. Cl. ......... 530/383; 530/412; 530/416; 530/417

(58) Field of Classification Search .................. None
See application file for complete search history.

(56) References Cited

FOREIGN PATENT DOCUMENTS

| WO | WO 96/15140 | 5/1996 |
|---|---|---|
| WO | WO 2005/014621 | 2/2005 |
| WO | WO 2006/067230 | 6/2006 |
| WO | WO 2006/103258 | 10/2006 |
| WO | 2009/156430 A1 | 12/2009 |

OTHER PUBLICATIONS

Girot P. et al., "2-Mercapto-5-Benzimidazolesulfonic Acid: An Effective Multimodal Ligand for the Separation of Antibodies," Journal of Chromatography B: Biomedical Sciences and Applications, vol. 808, No. 1, Aug. 25, 2004, pp. 25-33.
Mowry M. C. et al., "Production and Purification of a Chimeric Monoclonal Antibody Against Botulinum Neurotoxin Serotype A," Protein Expression and Purification, vol. 37, No. 2, Oct. 2004, pp. 399-408.
Coulon D. et al., "Penicillin Acylase Purification with the Aid of Hydrophobic Charge Induction Chromatography," Journal of Chromatography B: Biomedical Sciences and Applications, vol. 808, No. 1, Aug. 25, 2004, pp. 111-115.
Bengio S. et al., "Validated Alternatives to Protein A Sorbents for Antibody Production," Product Information from Biosephra/ Ciphergen [online], Mar. 2003, pp. 1-8, http://wolfson.huji.ac.il/ prification/pdf/hcic/biosepra_mbi_hypercell.pdf.
"Capto MMC/ Data File 11-0035-45 AA," Product Information from GE Healthcare [online], 2005, pp. 1-6, http://www.gelifesciences.co. jp/catalog/pdf_attach/11003545AA.pdf.
Nordfang et al., Thrombosis and Haemostasis, "FVIII Subunits: Purification and Antigenic Properties", 1987, vol. 58, No. 4, pp. 1043-1048.
Casademunt E et al., "The first recombinant human coagulation factor VIII of human origin: human cell line and manufacturing characteristics," European Journal of Haematology, 2012, vol. 89, pp. 165-176.

*Primary Examiner* — Marsha Tsay
(74) *Attorney, Agent, or Firm* — Teresa Chen

(57) ABSTRACT

A method for purifying a recombinant protein using a multimodal or mixed mode resin containing ligands which comprise a hydrophobic part and a negatively charged part is described. The invention is advantageous in that it is a single step chromatographic process which does not require adjustment of pH or conductivity during loading step and results in high yield and potency. The process is used for the purification of recombinant compositions of coagulation factor, particularly recombinant Factor VIII.

16 Claims, 5 Drawing Sheets

PURIFICATION OF FACTOR VIII USING A MIXED-MODE OR MULTIMODAL RESIN

CROSS-REFERENCE TO RELATED APPLICATIONS

This application is a 35 U.S.C. §371 national stage application of International Patent Application PCT/EP2008/059094 (published as WO 2009/007451), filed Jul. 11, 2008, which claimed priority of European Patent Application 07112287.3, filed Jul. 11, 2007; this application further claims priority under 35 U.S.C. §119 of U.S. Provisional Application 60/950,120, filed Jul. 17, 2007.

FIELD OF THE INVENTION

The present invention is related to a method for purifying a recombinant protein using a multimodal or mixed mode resin containing ligands which comprise a hydrophobic part and a negatively charged part. The protein of interest is a coagulation factor, particularly relevant to the purification of compositions of recombinant Factor VIII.

BACKGROUND OF THE INVENTION

Human Factor VIII, also known as antihaemophilia factor or FVIII:C is a human plasma protein consisting of two polypeptides with light chain molecular weight of 80,000 daltons and a heavy chain molecular weight variable from 90,000 to 220,000. It is considered as one of the key cofactors in the coagulation pathway necessary for the conversion of Factor X into its active form Factor Xa. Factor VIII circulates in plasma as a non-covalent complex with von Willebrand Factor (also known as FVIII:RP). Hemophilia, a bleeding disorder is caused due to abnormal levels of Factor VIII. Factor VIII levels below 20% normal may result in hemophilic condition in humans. A drop in the levels of less than 1% of Factor VIII leads to severe bleeding disorder, with spontaneous joint bleeding being the most common symptom.

The structure and biochemistry of recombinant factor VIII have been described previously.

Traditionally, isolation and purification of Factor VIII has been from a plasma derived source (cryoprecipitate). Purification procedures from plasma-derived sources include those exploring the use of immunoaffinity purification using polyclonal and monoclonal antibodies for the purification of FVIII. However, there may be instances where the Factor VIII effluent contains some residual antibody due to leaching from the support matrix, which may result in antigenicity during ultimate use, i.e when introduced into human or animal system. Purification procedures exploring the use of ion exchange chromatography on e.g. agarose beads have also been used for purification of factor VIII from plasma. These methods, however, often suffer from certain levels of contamination of the resulting FVIII:C.

However, purification of Factor VIII from genetically engineered recombinant source has gained importance in the past decade. Protein recovery and concentration of the final product is of utmost importance in the separation of recombinant proteins. The contaminants in recombinantly produced protein may include secreted proteins in the culture medium, media components, cell lysates, unwanted proteins produced by the cells and the nucleic acids.

When purifying a recombinant protein, the aqueous source materials in which the polypeptides of interest are found are furthermore often seen to be contaminated with one or more viruses. Techniques for inactivating viruses in polypeptide mixtures are known in the art, such as e.g. chemical methods, using solvent/detergent solutions, irradiation methods, or thermal methods, but attempts to combine such techniques with known polypeptide purification processes have produced methods with a multiplicity of steps unsuitable for large-volume production. It is also important to exert caution in that the used viral-inactivating agents do not denature the protein or are difficult to separate from the protein of interest. These agents have, however, been either denaturing or difficult to separate from the polypeptide of interest, and have required a special treatment or separation step. Other conventional methods for treating polypeptide-containing preparations for potential viral contamination, such as heat or irradiation, have resulted in either significant denaturation of the polypeptide of interest and/or insufficient inactivation of viruses. Many of the commercially available recombinant Factor VIII products (Advate®, Helixate®, Kogenate FS®, ReFacto®) are made using immunoaffinity chromatography including a detergent for purification and viral inactivation.

In the purification of therapeutic proteins produced by a recombinant DNA technique, it is well known that considerable problems are encountered when trying to reduce the content of DNA and Host Cell Protein (HCP) to the desired very low level.

Nordfang et al. (Thrombosis and Haemostasis 58(4), 1043-1048 (1987) describes a separation using an antibody resin and a buffer containing 50% ethylene glycol and high salt.

The purification of a recombinant protein expressed in mammalian cell system is typically performed in several steps. The different steps are usually separated into capture, intermediate and polishing. The objective of the capture step is two-fold; a) to obtain the target protein in a stable solution form and b) to reduce the volume (i.e. obtaining a solution concentrated with respect to protein content compared to the solution loaded onto the column ("the loading").

The latter step (reduction of volume) is critical to facilitate the subsequent steps of purification. The capture step is commonly achieved by using chromatography with an ion-exchange resin. The drawback of using an ion-exchange resin is that the conductivity and/or pH of the loading has to be adjusted. When the conductivity is adjusted, in most instances reduced, it is performed by addition of water which increases the volume of the starting material, making it impractical for subsequent steps and overall cumbersome for production purposes. Furthermore, adjustment of pH often results in the formation of aggregates which could interfere with the performance of the purification steps.

After the capture step, an intermediate purification may follow, which removes most of the significant impurities including DNA, viruses and endotoxins. These impurities can also be remove/reduced in capture. The polishing step refers to a final purification step, wherein trace contaminants and impurities are removed and the yield is an active biological product. Contaminants removed during the polishing step are often conformers of the target molecule or suspected leakage products.

There is still a need in the art for improved purification methods which are fast and efficient and wherein Factor VIII activity is essentially retained.

The method of the present invention is advantageous in that it, in a single step, provides a volume reduction and a considerable increase in specific activity. Thus, the method, in a single step, combines a capture and a purification step.

The present invention also provides an efficient process for producing a highly concentrated and very pure solution of recombinant Factor VIII wherein the Factor VIII protein is stabilized against degradation. With the present invention, it is possible to combine a capture and purification step without risking severe destabilization of the FVIII molecules and, in a single step, obtain an initial purification of the crude sample, obtain a substantial volume reduction (thereby facilitating further purification steps) as well as obtain a substantial purification factor (increase in FVIII specific activity) and a resulting solution ("capture pool") wherein the protein is stabilized against degradation.

SUMMARY OF THE INVENTION

The instant invention is related to the novel and efficient purification of recombinant proteins, especially coagulation factor VIII. The inventors of the present invention have found that use of multimodal columns for the capture of factor VIII molecules from mammalian cell culture fluid is a surprisingly fast and efficient purification method for removing contaminants from FVIII protein harvested from the culture, without the loss in the activity of the protein.

In one aspect, the invention provides a method of purifying a coagulation Factor VIII protein containing one or more contaminants, the method comprising the steps of:

(a) contacting the Factor VIII protein with a multimodal or mixed mode resin containing ligands which comprise a hydrophobic part and a negatively charged part;

(b) eluting said Factor VIII protein with an elution buffer containing at least 1.5 M salt and at least 40% (w/v) of ethylene glycol, propylene glycol, or a mixture thereof, and calcium ions.

In different embodiments, the method further comprises a step (c) wherein the Factor VIII-containing solution resulting from step (b) is collected; and/or the method further comprising a step (a1) wherein the column, subsequent to step (a) and before step (b), is passed with one or more wash buffer(s).

In various embodiments thereof, one or more of said wash buffer(s) comprise(s) 10 mM to 1000 mM salt, and/or the elution buffer of step (b) contains at least 2M salt and at least 45% (w/v) of ethylene glycol, propylene glycol, or a mixture thereof, such as, e.g. 2.3-2.6 M salt and 48-52% (w/v) of ethylene glycol, propylene glycol, or a mixture thereof; and/or the salt contained in the elution buffer of step (b) is selected from: NaCl, $NH_4Cl$, KCl, $(NH_4)_2SO_4$, $CH_3CO_2NH_4$, or a mixture of two or more of these.

In another aspect, the invention provides a single step method of purifying a Factor VIII protein containing one or more contaminants, comprising the steps of:

a) contacting the protein with a multi-modal resin containing the ligands which comprise a hydrophobic part and a negatively charged part;

b) eluting the said protein with an elution buffer containing at least 1.5 M salt and at least 40% (w/v) of ethylene glycol, propylene glycol, or a mixture thereof, and calcium ions;

wherein the said method achieves a reduction in the column volume of about 250-fold.

In another aspect, the invention provides a single step method of purifying a Factor VIII protein containing one or more contaminants, comprising the steps of:

a) contacting the protein with a multi-modal resin containing the ligands which comprise a hydrophobic part and a negatively charged part;

b) eluting the said protein with an elution buffer containing at least 1.5 M salt and at least 40% (w/v) of ethylene glycol, propylene glycol, or a mixture thereof, and calcium ions;

wherein the said method achieves a "purification factor" of at least 30-fold.

In yet another aspect, the invention provides a method for stabilizing a Factor VIII protein, comprising the steps of:

a) contacting the protein with a multi-modal resin containing the ligands which comprise a hydrophobic part and a negatively charged part;

b) eluting the said protein with an elution buffer containing at least 1.5 M salt and at least 40% (w/v) of ethylene glycol, propylene glycol, or a mixture thereof, and calcium ions.

DESCRIPTION OF THE INVENTION

Figure 1A:
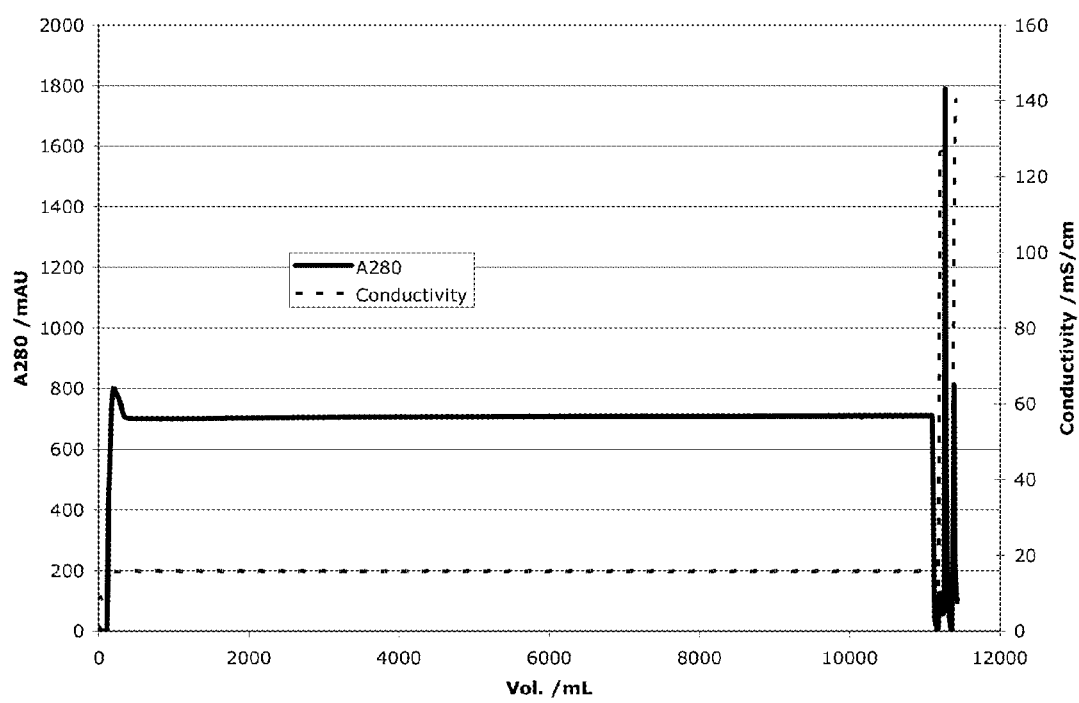
FIG. 1A is a chromatogram showing the UV absorption at 280 nm, conductivity and pH over a purification run with equilibration, loading, wash and elution.

The present method of purifying coagulation factor VIII is performed by using multimodal chromatography making use of resins that are both hydrophobic and negatively charged. The solution of the protein to be purified, e.g. the protein-containing supernatant obtained from mammalian cell fermentation, is applied to the multimodal resin by passing a solution over a chromatography column containing said resin. The solution (loading) is typically filtered (e.g. by dead-end filtration or cross flow filtration) and/or centrifuged to remove cells and particles before being loaded onto the resin. The loading step does not require adjustment of pH or conductivity. After loading, the column is typically washed with one or more wash buffers, one of which containing high concentration of salt. In one embodiment, the column is washed, after loading, with equilibration buffer, optionally followed by wash with a second buffer with high concentration of salt.

To recover adsorbed substances, elution is performed by passing an elution buffer comprising a high concentration of salt and an organic solvent over the column.

The invention provides a column volume (CV) reduction of about 250-fold, compared to (and calculated from) the volume of the loading sample, thus achieving an excellent volume reduction. By "volume reduction" is meant a reduction in the volume of protein-containing eluate solution when compared to the volume of protein-containing loading solution (e.g. the clarified crude sample from the fermentation process).

The purification method of the invention further provides a protein yield of 70-100% and the purification factor (increase in the specific activity) is up to 100-fold. The resultant purified protein is stable in the elution buffer for at least 2 months at −70° C.

Furthermore, the method of the invention provides a stable factor VIII solution: The capture eluate can be frozen and thawed at least 3 times without significantly loss of activity.

The invention makes use of multi-modal chromatography resins for the separation of the factor VIII protein of interest from the contaminants. The multi-modal chromatography, wherein two or more different, but co-operative, sites interact with a target, has been determined to be an appropriate system for purification of factor VIII protein. The chromatography resin used for the purification of the recombinant protein in the present invention is commercially available, for example: Capto MMC™ (GE Healthcare) or MBI HyperCel™ (Pall, formerly BioSepra).

Capto MMC contains a ligand with multimodal functionality that gives a different selectivity compared to traditional ion exchangers and also provides the possibility of binding proteins at salt concentrations as high as 0.5M to 1.0 M. The ligand herein exhibits diverse functionalities for interaction with the target molecule and thus offers ionic interaction, hydrogen bonding and hydrophobic interaction. In one embodiment of the invention, the multimodal resin is Capto MMC™.

MBI HyperCel™ (Pall), yet another multimodal chromatography, is efficient in tackling stability problems and leakage from protein-based affinity columns. More specifically, MBI Hypercel® (Pall), an adsorbent comprising mercapto-benzimidazole-sulphonic acid ligands, provides hydrophobic as well as ionic interactions with a given protein. The hydrophobic interactions are assumed to be due to the aromatic ring system, while the ionic interactions should be due to the $SO_3^-$ substituent, which is known as a strong cation exchanger. In addition, the nitrogen atoms of the aromatic system of the MBI ligand are chargeable under certain conditions, and can consequently provide ionic interactions with negatively charged groups.

In an advantageous embodiment, the contaminants are adsorbed to the multimodal ligands, and an essentially pure fraction of coagulation factor VIII is recovered by a subsequent selective elution. The capture step provides a purification factor (increase in specific activity) of at least 80 times, such as 80 to 100-fold, 90 to 100-fold or 100-160-fold The resulting capture pool comprises the factor VIII protein that is at least 10% pure, such as at least 20% or about 30% to 60%, such as 30% to 50%. The purity is defined at the amount of factor VIII protein in % (w/w) (e.g. as determined by ELISA) of the total amount of protein.

In one embodiment of the present method, the solution loaded to the multi-modal chromatography resin is a factor VIII-containing harvest from mammalian cell fermentation. In one embodiment thereof, said harvest is filtered and/or centrifuged to remove cells and particles; in another embodiment the harvest is loaded to the resin without any adjustment of pH or conductivity of the loading solution.

The present invention specifically encompasses a method wherein the loading step comprises loading the protein-containing loading solution onto the resin at a pH and conductivity similar to the pH and conductivity a factor VIII-containing harvest from mammalian cell fermentation, optionally a filtered harvest.

This provides greater advantage in the initial capture step by restricting the volume which otherwise is necessary to adjust (reduce) the conductivity of the loading solution.

In one embodiment, the Factor VIII-containing harvest is stabilized by the addition of imidazol (such as, e.g., 1-10 mmol imidazol per L harvest). Due to the small amount and volume of added imidazol compared to the volume of the harvest, any change in pH and/or conductivity of the harvest is negligible. In a further embodiment, the harvest is then (i) filtered and/or centrifuged to remove cells and particles and (ii) loaded to the resin without further addition of chemicals.

The method of the invention is typically performed in a number of steps: equilibration of column, loading and elution. One or more washing steps may be included after loading and before elution. The washing step(s) is/are typically done using at least one buffer containing a high concentration of salt. In one embodiment, a wash step is employed using a buffer comprising 10 mM to 1000 mM salt, such as, e.g. 100-1000 mM, or 250-1000 mM, or 500-1000 mM, or 500-800 mM salt. In another embodiment, the method includes a washing step wherein, after loading, the column is first washed with equilibration buffer and then washed with a second washing buffer containing high salt.

In one embodiment, the equilibration buffer comprises a buffering agent (such as e.g. imidazole in the range of 5 mM to 100 mM, e.g. 20 mM Imidazole), a Ca-salt (1 mM to 100 mM, e.g. 10 mM $CaCl_2$,) a detergent (such as e.g. Tween™ 80 in the range of 0.001% to 0.1%, e.g. 0.02% (w/v) Tween™ 80) and a salt (10 mM to 1000 mM, e.g. 50 mM NaCl). The equilibration buffer is maintained at a pH of 6.0 to 8.0; preferably the pH conditions are maintained at 7.3 to 7.5. It will be appreciated by a person skilled in the art that the factor VIII protein exemplified herein is stable at a pH of about 6.0 to 8.0 and thus the equilibration buffer is at a pH of 7.3-7.5, more preferably at 7.5.

In one embodiment, the wash buffer comprises a buffering agent (such as e.g. imidazole in the range of 5 mM to 100 mM, e.g. 20 mM Imidazole), a Ca-salt (1 mM to 100 mM, e.g. 10 mM $CaCl_2$,) a detergent (such as e.g. Tween™ 80 in the range of 0.001% to 0.1%, e.g. 0.02% (w/v) Tween 80) and a salt (e.g. NaCl in the range of 50 mM to 1000 mM).

The elution step is performed with an elution buffer comprising at least 1.5 M salt and at least 40% (w/v) of ethylene glycol, propylene glycol or a mixture thereof, and calcium ions (1 mM to 100 mM, e.g. 10 mM $CaCl_2$). The elution buffer has a pH of 6.0 to 8.0; preferably the pH conditions are maintained at 7.3 to 7.5. To maintain the desired pH conditions, the elution buffer also contains a buffering agent.

The term "buffering agent" encompasses those agents which are able to maintain the pH of a solution within a desired range—in the context of the present invention within the range of 6.0 to 8.0, such as 7.3 to 7.5. The buffer concentration range is chosen to maintain the preferred pH of the solution. The buffering agent may also be a mixture of at least two buffering agents, wherein the mixture is able to provide a pH value in the specified range. Buffering agents may include, but are not limited to, citrate (sodium or potassium), acetate (ammonium, sodium or calcium), histidine (L-histidine), phosphate (sodium or potassium), tartaric acid, succinic acid, MES, HEPES, imidazol, TRIS, ethanolamine, and mixtures of two or more thereof. In one embodiment, the buffering agent employed is imidazole in the range of 5 mM to 100 mM.

Preferred salts are NaCl, $NH_4Cl$, KCl, $(NH_4)_2SO_4$, $CH_3CO_2NH_4$ (ammonium acetate, $NH_4$ Ac), or a mixture of two or more thereof. In one embodiment, the elution buffer comprises about 2.5 M salt and at least 40% glycol; in another embodiment, the elution buffer comprises about 2.5M salt and about 50% glycol. In one embodiment, the salt is NaCl; in another, the salt is $NH^4Cl$. In one embodiment, the glycol is ethylene glycol; in another, the glycol is propylene glycol. In yet another embodiment, the elution buffer comprises NaCl and ethylene glycol.

In another embodiment, $NH_4Cl$ at a concentration of 2.5M with ethylene glycol is also used for elution of the protein. In yet another embodiment, the elution buffer further comprises a detergent. In a particular embodiment of the method, the eluent is 20 mM Imidazole, 10 mM CaCl$_2$, 0.02% (v/v) Tween 80, 2.5M NaCl and 8 M ethylene glycol at a pH of 7.5.

In another embodiment, MBI HyperCel™ resin is used in the method for purification of Factor VIII. In one embodiment, binding of the recombinant factor VIII using the MBI HyperCel™ column is performed after addition of 100 mM Na$_2$SO$_4$ to the harvest and elution is achieved with 1M NaCl and 5M glycerol.

In a particular embodiment of the invention, the method comprises the steps of:

a) contacting the Factor VIII with a multimodal or mixed mode resin containing the ligands which comprise a hydrophobic part and a negatively charged part;

b) passing the column with equilibrating buffer comprising 20 mM Imidazole, 10 mM CaCl$_2$, 0.02% (w/v) Tween 80 and 50 mM NaCl and wash buffer comprising of 20 mM Imidazole, 10 mM CaCl$_2$, 0.02% (w/v) Tween 80 and 1.5M NaCl;

c) eluting the said protein with elution buffer comprising 20 mM Imidazole, 10 mM CaCl$_2$, 0.02% (v/v) Tween 80, 2.5M NaCl, and 8M ethylene glycol.

The first step of the purification of a recombinant protein expressed in mammalian cells, under most normal circumstances, handles large loading volumes. For commercial protein purification, it is important to reduce the volume to where it can be easily handled. Furthermore, the purification step has to have a significant yield to achieve process economy for commercial or other purposes. About 20 to 100 times reduction in volume in the first step is normally aimed at in the first step of the protein purification wherein the latter is regarded as a sound volume reduction.

In one embodiment, the loading volume containing the protein to be purified is above 500 column volumes (CV). The protein eluted provides a reduction in the final volume of more than 100-fold. The instant invention encompasses a loading volume of 50-600 CV. The reduction in volume is preferably about 100-300 times. In one embodiment, the loading volume is about 500 CV, or about 450-600 CV, and the factor VIII protein is eluted in about 2 CV achieving a volume reduction of about 250 times.

In another embodiment, the capture step can be combined with one or more virus inactivating agents, such as e.g. Triton X-100 (for example in a concentration of about 1% (w/v). The virus inactivating agent may e.g. be added to one or more of the used buffers.

Flow rates are manipulated to be between 300-950 cm/hr for all steps of the purification process except elution and clean-in-place (CIP) steps where flow rates are at 30-350 cm/h. In one embodiment the flow rate at loading is 450 cm/h; during elution and CIP, the flow rate is decreased to 30 cm/h. In one embodiment of the invention, the flow rate at loading is about 450-600 cm/h.

In one aspect, the invention also relates to a preparation comprising:

(i) a Factor VIII protein; and (ii) a buffer containing at least 1.5 M salt and at least 40% (w/v) of ethylene glycol, propylene glycol, or a mixture thereof, and calcium ions;

wherein the Factor VIII is 30% to 60% pure.

DEFINITIONS

In the present invention, "Factor VIII protein" is meant to include full-length factor VIII, FVIII:C, and deletion derivatives of full-length factor VIII having coagulant activity. By deletion derivative, it is meant factor VIII wherein the whole or part of the B-domain is missing while the coagulant activity is retained. Such B-domain deleted forms of Factor VIII are, for example, described in WO91/09122. The structure and biochemistry of Factor VIII in general have been described by Kaufman (*Trends in Biotechnology*, 9, p. 353-359 (1991) *and Hematology*, 63, p. 155-165 (1991)). Included are also factor VIII sequence variants and derivatives, including pegylated, acylated, and polysialylated forms of factor VIII, having maintained the characteristic factor VIII biological activity. The factor VIII may be obtained by recombinant means. In one embodiment, the factor VII is recombinantly produced factor VIII. In one embodiment, the Factor VIII is full length Factor VIII; in another embodiment, the Factor VIII protein is a B-domain deleted Factor VIII. In yet another embodiment, the factor VIII is a pegylated, acylated, or polysialylated Factor VIII.

Factor VIII concentrates derived from human plasma contain several fragmented fully active Factor VIII forms as described by Andersson et al (*Proc. Natl. Acad. Sci. USA*, 83, p. 2979-2983 (1986)). The smallest active form has a molecular mass of 170 kDa and consists of two chains of 90 kDa and 80 kDa held together by metal ion(s) (see, e.g. EP197901). Such Factor VIII fragments are also included—purification of such fragments constitute one embodiment of the present invention.

Biological activity of factor VIII are assayed, e.g., as described in Experimental section (see below).

The term "eluent" is meant in its conventional meaning as it is identified in the art which is a buffer or buffers of suitable pH and/or ionic strength to release one or more proteins or compounds from a separation matrix.

As used herein, the "salt" in the elution step refers to an alkaline earth, alkali metal, or ammonium salt, i.e., a salt having a cation from the alkaline earth or alkali metal elements or an ammonium cation and having an inorganic or organic (hydrocarbon-based) anion. Examples of such salts include sodium chloride, ammonium chloride, sodium citrate, potassium citrate, potassium chloride, magnesium chloride, calcium chloride, sodium phosphate, calcium phosphate, ammonium phosphate, magnesium phosphate, potassium phosphate, sodium sulfate, ammonium sulfate, potassium sulfate, magnesium sulfate, calcium sulfate, etc. Preferred salts herein are chlorides or sulfates. The most preferred salt herein is sodium chloride.

The term "multi-modal chromatography ligand" refers to a ligand that is capable of providing at least two different, but co-operative, sites which interact with the protein to be bound. One of these sites gives an attractive type of charge-charge interaction between the ligand and the substance of interest. The other site typically gives electron acceptor-donor interaction and/or hydrophobic and/or hydrophilic interactions. The present invention is directed, particularly to the hydrophobic interactions. Electron donor-acceptor interactions include interactions such as hydrogen-bonding, .pi.-.pi., cation-.pi., charge transfer, dipole-dipole, induced dipole etc. Multi-modal chromatography ligands as used herein or elsewhere are also known as "mixed mode" chromatography ligands.

The term "capture step" refers, in the context of liquid chromatography, to the initial step of a separation procedure. Most commonly, a capture step includes clarification, concentration, stabilization and a significant purification from soluble contaminants. After the capture step, an intermediate purification may follow, which removes most of the significant impurities including DNA, viruses and endotoxins. These impurities can also be remove/reduced in capture.

The term "polishing step" refers to a final purification step, wherein trace contaminants and impurities are removed and the yield is an active biological product. Contaminants removed during the polishing step are often conformers of the target molecule or suspected leakage products.

The term "Column Volume" as known in the art of chromatography refers to the geometric volume of the part of the tube that contains the packing. As per the instant invention, the loading volume is above 50 Column Volumes (CV) or more or less about 300-600 CV or 450-600 CV. The protein eluted at the final step of purification is about 2-5 CV achieving a volume reduction of about 100-fold to 350-fold, such as, e.g., 250-fold.

The "purification factor" is defined as increase in specific activity: That is U/mg protein before the purification step compared to U/mg protein after the purification step. The specific activity of coagulation factor VIII may be assayed by commercially available activity assays, such as, for example, using CoaTest® Chromogenix™ (Instrumentation Laboratory, Belgium) according to the manufacturer's protocol or as described in the Experimentals section, below.

The term "a single step method" refers to a method of purifying a Factor VIII protein containing one or more contaminants, wherein the method achieves both a reduction in volume and an increase in specific activity (purification factor>1).

In one embodiment of the present invention, the method provides (i) a reduction in the column volume of about 250-fold, and (ii) a "purification factor" of at least 30-fold.

The invention is more fully understood by reference to the following examples. These examples should not, however, be construed as limiting the scope of the invention.

Examples

The structure and biochemistry of recombinant factor VIII have been described previously. (See, e.g. Trends in Biotechnol. 1991, 9:353-359, Transfus. Med. Rev. 1992, 6:235-246).

Furthermore, isolation of factor VIII as well as recombinant production of factor VIII (full-length and variants/truncated forms) are described in the art:

Recombinant DNA technology has allowed construction of plasmids that direct the expression of fusion products of Factor VIII protein in transfected mammalian cells. Recombinant production of Factor VIII in cell culture is reported by Wood et al (See Nature, 1984, 312:330-337). Active variants and analogs of Factor VIII protein and DNA sequences encoding them have also been reported (U.S. Pat. No. 4,868,112, EP0786474, WO 86/06101, and WO 87/07144). Various manipulations of the genetic sequences have shown that the B domain of the Factor VIII is not critical for the procoagulant activity and the active procoagulant protein can be expressed by expressing the Factor VIII-encoding the nucleotide region that lacks the B domain. Important modifications in such variants and analogs include that part or all of the B domain are missing and/or specific amino acid positions are modified, for example, such that normally protease-labile sites are resistant to proteolysis, e.g. by thrombin or activated Protein C. Other analogs include modification at one or more lysine and/or tyrosine residues. The truncated form of the protein is a 170 kDa glycoprotein consisting of 1438 amino acids. This B-domain deleted protein is a post-translational modification of the plasma-derived Factor VIII and is comparable in its anti-hemophilic activity to that of the parent.

Factor VIII Activity Assay

Assays for estimating biological activity of factor VIII are well known to the skilled person and such assays are commercially available from a number of providers.

The activity of purified Factor VIII may e.g. be assayed using CoaTest® Chromogenix™ (Instrumentation Laboratory, Belgium) according to the manufacturer's protocol.

Example 1

Recombinant production of Factor VIII is well known in the art; reference can, for example, be made to U.S. Pat. No. 5,633,150 (Genentech) and U.S. Pat. No. 7,138,505 (Novo Nordisk/Novartis).

The recombinant Factor VIII was expressed in CHO-cells in a commercially available serum free media. The protein harvest from the fermentation was further used for the purification.

Example 2

Purification of Recombinant Factor VIII

Capto MMC (GE Healthcare, Uppsala, Sweden) resin was used for the purification of the recombinant protein. The column was packed with a bed height of 12 cm and 24 ml bed volume.

As a first step, the purification process involved loading wherein the harvest from the fermentation was applied onto the column. The column volume (CV) of loading was 450 CV (Table 1). This was followed by passing the column with equilibration buffer consisting of 20 mM imidazole, 10 mM CaCl2, 0.02% (v/v) Tween 80 and 50 mM NaCl. The pH of the equilibration buffer is adjusted to 7.5. The column is further washed with wash buffer (20 mM imidazole, 10 mM CaCl2, 0.02% (v/v) Tween 80 and 1.5M NaCl) at a pH equivalent to the equilibration buffer, i.e. 7.5. The column volumes of equilibration and washing steps were 3 CV (Table 1).

TABLE 1

Column Volumes (CV) used in various steps of Factor VIII purification

| Step | Buffer | Column Volume |
|---|---|---|
| Equilibration | Equilibration Buffer | 3 |
| Loading | Loading | 450 |
| Wash 1 | Equilibration Buffer | 3 |
| Wash 2 | Wash Buffer | 3 |
| Elution | Elution Buffer | 5 |
| CIP | CIP | 3 |

Elution was carried out by passing elution buffer onto the column. Elution buffer consists of 20 mM imidazole, 10 mM $CaCl_2$, 0.02% (v/v) Tween 80 and 2.5M NaCl and 8M ethylene glycol.

Flow rate was maintained at 450 cm/h at every step of purification except the elution and CIP during which the flow rate was 30 cm/h.

Figure 1B:
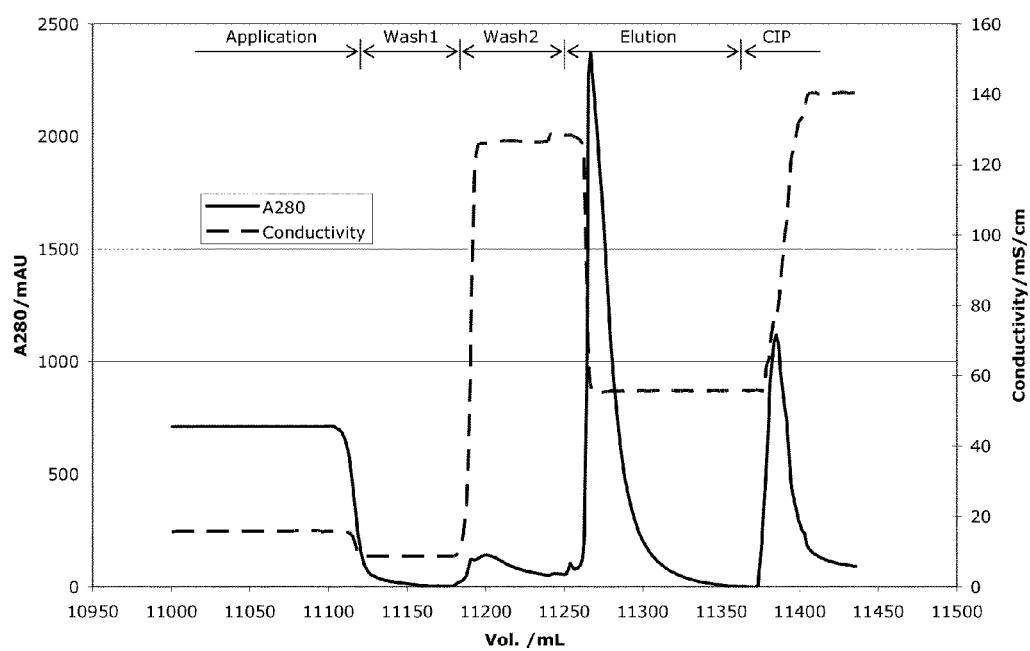
FIG. 1B shows an enlargement of the wash and elution part of the chromatogram of FIG. 1.

A chromatogram showing the UV absorption at 280 nm over a purification run with equilibration, loading, wash and elution is provided in FIG. 1.

Example 3

Activity Assay

The activity of purified Factor VIII was measured using a modification of the CoaTest® SP assay:

Reagents and buffer stock solution from the CoaTest® SP kit were used. All reagents were allowed to reach room temperature before initiation of experiment. Samples were diluted in CoaTest assay buffer (50 mM Tris, 150 mM NaCl, 1% BSA, pH 7.3, with preservative) to approximately 2 mU/ml. The reference plasma was diluted in assay buffer to 5-0.5 mU/ml. The samples were diluted in assay buffer to 12 and 9 U/ml, then 10-fold in FVIII-deficient plasma with VWF (Dade Behring), and finally 10- and 20-fold in CoaTest® assay buffer (resulting in 4 dilutions per sample). Fifty µl of samples, standards, and buffer negative control were added to 96-well microtiter plates (Nunc) in duplicates. The factor IXa/factor X reagent, the phospholipid reagent and CaCl2 from the CoaTest® SP kit were mixed 5:1:3 (vol:vol:vol) and 75 µl of this added to the wells. After 15 min incubation at room temperature 50 µl of the factor Xa substrate S-2765/ thrombin inhibitor I-2581 mix was added and the reactions incubated 10 min at room temperature before 25 µl 2% citric acid was added. The absorbance at 415 nm was measured on a Spectramax® microtiter plate reader (Molecular Devices) with absorbance at 620 nm used as reference wavelength. The value for the negative control was subtracted from all samples and a calibration curve prepared by linear regression of the absorbance values plotted vs. FVIII concentration in mU/ml.

ELISA Assay

Factor VIII antigen was determined using the commercial ELISA kit from Affinity Biologicals (VisuLize Factor VIII Antigen Kit, Lot AG8-0006) essentially as described by the manufacturer.

Recombinant Factor VIII was purified from the fermentation harvest as described in Example 2, above. Purification factor and yield of Factor VIII protein was determined by CoA and ELISA as described above:

specific activity from 0.0046 mg Factor VIII/mg total protein to 0.6 mg Factor VIII/mg total protein e.g. obtain a purification factor of 130 times determined by ELISA.

Example 4

Protein Gel Electrophoresis

SDS gel electrophoresis was carried out using 7% NuPage® tris acetate gel with tris acetate as running buffer essentially as described by the manufacturer (Invitrogen). Briefly, the gel electrophoresis was carried out for 50 min at 150 volt and the samples were stained with SilverQuest® staining kit (Invitrogen) as described in the manufacturer's instructions. The molecular weight (MW) standards used were Mark 12 from Invitrogen.

Figure 2:
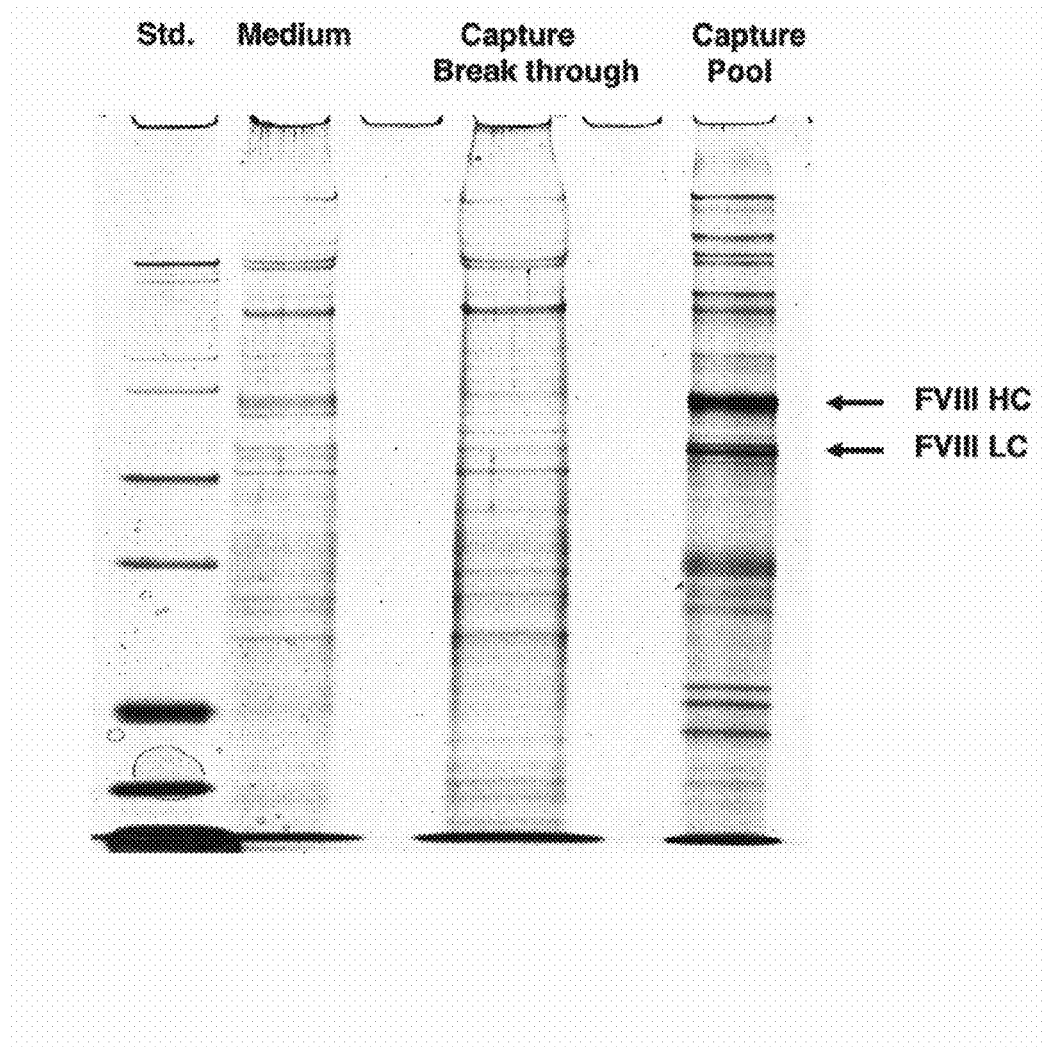
FIG. 2 shows a silver-stained SDS gel electrophoresis illustrating the purification obtained using the Capto MMC column in the purification steps of loading, flow through (FT) and elution. Lane 1: MW standard, Lane 2: Cell culture medium, Lane 3: Empty, Lane 4: Break through (not bound material) from the Capto MMC column, Lane 5: Empty, Lane 6: Capture pool (protein material bound and eluted from the Capto MMC column FIG. 3 is a histogram showing the percentage yields of recombinant Factor VIII purified using Capto MMC resin with different elution buffers containing various concentrations of NaCl or $NH_4Cl$ and ethylene glycol.

The results as shown in FIG. 2 reveal a very high enrichment of the recombinant Factor VIII in the capture pool illustrated by the presence of high amount of the heavy chain (HC) and light chain (LC) bands (indicated by arrows in the FIG. 2).

Example 5

Purification Visualised by SDS-Gel Electrophoresis

Protein samples for electrophoresis were denatured and reduced at 70° C. for 10 min in LDS sample buffer (Invitrogen) containing 50 mM DTT. Separation gels were 7% tris-acetate (TA) Pre-Cast Novex polyacrylamide gel (Invitrogen)

TABLE 2

Purification factor and yield (determined by CoA test)

| Step | Volume [ml] | Activity [U/ml] | Activity total [U] | Protein [mg/ml] | Protein total [mg] | Specific activity [U/mg] | Purification factor [X] | Overall Yield [%] |
|---|---|---|---|---|---|---|---|---|
| Medium | 11000 | 117 | 1287000 | 2.11 | 23221 | 55 | 1 | 100.0 |
| Capture flow-through | 11000 | 1.8 | 19800 | 2.10 | 23100 | | | 1.5 |
| Capture pool | 45 | 14204 | 639180 | 2.68 | 120.6 | 5300 | 96 | 49.7 |

As can be seen from the above results it is possible to concentrate FVIII-containing medium from 11000 ml to 45 ml (244 times) and at the same time obtain in increase in specific activity from 55 U/mg to 5300 U/mg e.g. obtain a purification factor of 96 times determined by activity measurement.

and electrophoresis was carried out for 60 min at a limiting voltage of 150 V and with tris-acetate buffer (Invitrogen) as both anode and cathode buffer. Silver staining was carried out using SilverQuest® (Invitrogen) according to the manufacturer's description.

TABLE 3

Purification factor and yield (determined by ELISA)

| Step | Vol. [ml] | Factor VIII protein [µg/ml] | Factor VIII protein total [mg] | Protein [mg/ml] | Protein total [mg] | "Specific activity" [mg Factor VIII/mg total protein] | Purification factor [X] | Yield [%] |
|---|---|---|---|---|---|---|---|---|
| Medium | 11000 | 9.7 | 106.7 | 2.11 | 23221 | 0.0046 | 1 | 100.0 |
| Capture flow through | 11000 | 0.6 | 6.6 | 2.10 | 23100 | 0.00028 | | 6.2 |
| Capture pool | 45 | 1706 | 76.8 | 2.68 | 120.6 | 0.6 | 130 | 72.0 |

As can be seen from the above results it is possible to concentrate FVIII containing medium from 11000 ml to 45 ml (244 times) and at the same time obtain in increase in The gel illustrate the large purification obtained using the Capture MMC column. The cell medium contains a series of proteins. The large majority of these protein pass through the column whereas the Factor VIII is highly concentrated in the capture pool from the column.

Example 6

Elution Conditions

Various elution conditions were tested for the Capto MMC resin. To the harvest containing recombinant Factor VIII, glycerol at 5% final concentration and CHAPS at 5 mM were added. Equilibration was carried out with equilibration buffer of 20 mM Imidazole, 10 mM $CaCl_2$, Tween 80 (0.2% v/v), 50 mM NaCl, 5 mM CHAPS and 5% glycerol at pH 7.5.

Figure 3:
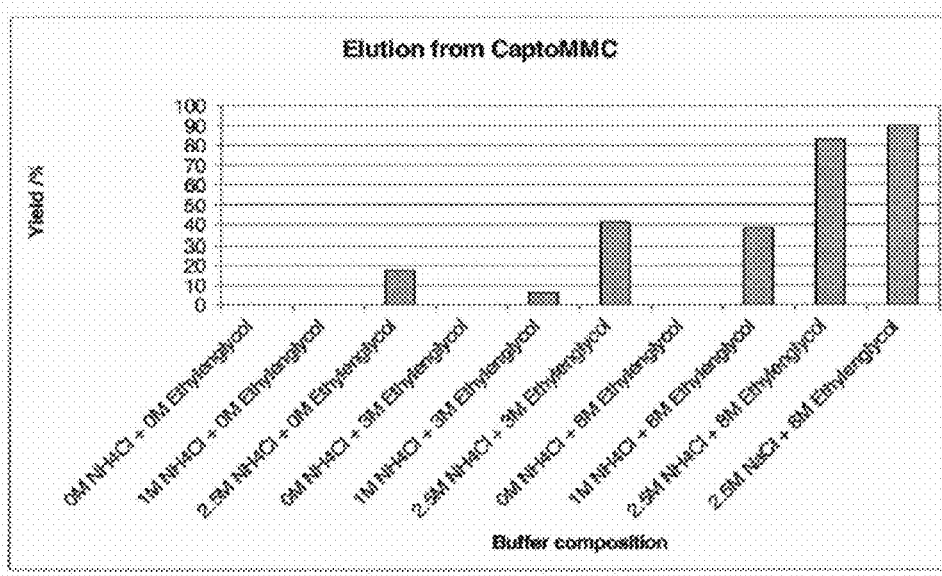
Figure 4:
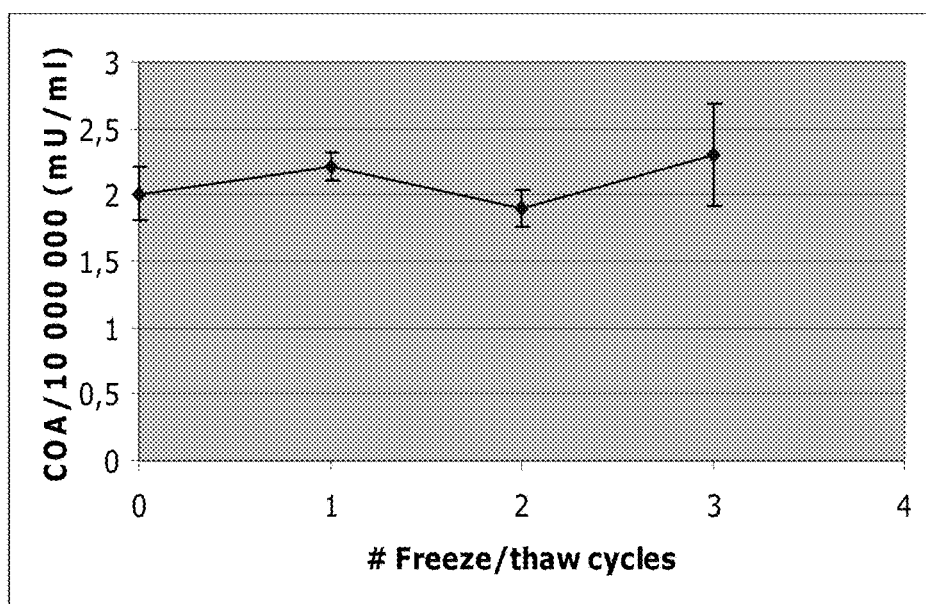
FIG. 4 shows the effect of repeated freeze/thaw cycles on the stability of the Factor VIII in the capture pool.

Elution buffer of 20 mM ethanolamine, 10 mM $CaCl_2$, Tween 80 (0.2% v/v), at pH 8.3 with different salt and ethylene glycol concentrations were used which include: a. no addition; b. 1M $NH_4Cl$; c. 2.5M $NH_4Cl$; d. 3M ethylene glycol; e. 1M $NH_4Cl$+3M ethylene glycol; f. 2.5M $NH_4Cl$+3M ethylene glycol; g. 8M ethylene glycol; h. 1M $NH_4Cl$+8M ethylene glycol; I. 2.5M $NH_4Cl$+8M ethylene glycol; 2.5M NaCl+8M ethylene glycol. The elution conditions were determined based on the percentage yield. FIG. 3 shows that at concentrations of 2.5M $NH_4Cl$ or 2.5M NaCl and 8M ethylene glycol, the percentage yield of the protein was maximum (FIG. 3).

Example 7

Freeze/Thaw Stability of Capture Pool

Aliquots of the capture pool, eluated from the Capto MMC resin as described in Example 2, were subjected to a number of freeze/thaw cycles, with freezing overnight at −80° C. followed by thawing at 4° C. the next day. Factor VIII activity was measured simultaneously for all samples using CoA assay (CoaTest® Chromogenix™, as described in Example 3) at the end of the experiment.

TABLE 4

Specific activity of Factor VIII in capture pool following repeated freeze/thaw cycles.

| | Freeze/thaw cycle 0 | Freeze/thaw cycle 1 | Freeze/thaw cycle 2 | Freeze/thaw cycle 3 |
|---|---|---|---|---|
| FVIII Activity (mU/ml) | 2 | 2.2 | 1.9 | 2.3 |

The invention claimed is:

1. A method of purifying a coagulation Factor VIII protein from a solution containing one or more contaminants, the method comprising: a single step method that captures and purifies the Factor VIII protein in the solution in one passage of the Factor VIII protein through a column, wherein said single step method comprises (a) contacting the Factor VIII protein solution with a column containing a multimodal or mixed mode resin containing ligands which comprise a hydrophobic part and a negatively charged part; and (b) eluting said Factor VIII protein with an elution buffer containing at least 1.5 M salt and at least 40% (w/v) of ethylene glycol, propylene glycol, or a mixture thereof, and calcium ions, to obtain a purified Factor VIII protein.

2. The method according to claim 1, further comprising a step (c) wherein the Factor VIII-containing solution resulting from step (b) is collected.

3. The method according to claim 1, further comprising a step (a1) wherein the column, subsequent to step (a) and before step (b), is passed with one or more wash buffer(s).

4. The method according to claim 3, wherein one or more of the wash buffer(s) comprise(s) 10 mM to 1000 mM salt.

5. The method according to claim 4, wherein the wash buffer contains 0.5-0.8 M salt.

6. The method according to claim 1, wherein the elution buffer of step (b) contains at least 2M salt and at least 45% (w/v) of ethylene glycol, propylene glycol, or a mixture thereof.

7. The method according to claim 6, wherein the elution buffer of step (b) contains 2.3-2.6 M salt and 48-52% (w/v) of ethylene glycol, propylene glycol, or a mixture thereof.

8. The method according to claim 1, wherein the salt contained in the elution buffer of step (b) is selected from: NaCl, $NH_4Cl$, KCl, $(NH_4)_2SO_4$, $CH_3CO_2NH_4$, or a mixture of two or more of these salts.

9. The method according to claim 8, wherein said elution buffer contains NaCl and ethylene glycol.

10. The method according to claim 1, wherein the elution buffer contains calcium ions in a concentration of 1 mM to 100 mM.

11. The method according to claim 1, wherein step (a) is performed:
(i) at a pH equivalent to the pH of a loading solution, and/or
(ii) without adjustment of conductivity.

12. The method according to claim 1, wherein the Factor VIII protein is selected from the group consisting of: full length Factor VIII, FVIII:C, B-domain deleted versions of Factor VIII, pegylated derivatives of Factor VIII, polysialylated derivatives of Factor VIII, and combinations thereof.

13. The method according to claim 1, wherein the elution buffer in step (b) contains 20 mM Imidazole, 10 mM $CaCl_2$, 0.02% (w/v) Tween 80, and 2.5M NaCl and 8M ethylene glycol at a pH of about 7.5.

14. The method according to claim 1, wherein the said method achieves a reduction in the column volume of about 250-fold.

15. The method according to claim 1, wherein the method achieves a purification factor of Factor VIII protein of at least 30-fold.

16. A method for stabilizing a Factor VIII protein, comprising a single step method that captures and stabilizes the Factor VIII protein solution in one passage of the Factor VIII protein through a column, wherein said single step method comprises
a) contacting the Factor VIII protein with a column containing a multi-modal or mixed mode resin containing ligands which comprise a hydrophobic part and a negatively charged part; and
b) eluting the Factor VIII protein with an elution buffer containing at least 1.5 M salt and at least 40% (w/v) of ethylene glycol, propylene glycol, or a mixture thereof, and calcium ions, to obtain stabilized Factor VIII protein.

* * * * *

UNITED STATES PATENT AND TRADEMARK OFFICE
CERTIFICATE OF CORRECTION

| | | |
|---|---|---|
| PATENT NO. | : 8,399,620 B2 | Page 1 of 1 |
| APPLICATION NO. | : 12/668530 | |
| DATED | : March 19, 2013 | |
| INVENTOR(S) | : Bang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 562 days.

Signed and Sealed this
Eleventh Day of March, 2014

Michelle K. Lee
*Deputy Director of the United States Patent and Trademark Office*